United States Patent [19]
O'Phelan et al.

[11] Patent Number: 5,876,424
[45] Date of Patent: Mar. 2, 1999

[54] ULTRA-THIN HERMETIC ENCLOSURE FOR IMPLANTABLE MEDICAL DEVICES

[75] Inventors: Michael J. O'Phelan, Oakdale; Farrell Oleen, Princeton, both of Minn.

[73] Assignee: Cardiac Pacemakers, Inc., St. Paul, Minn.

[21] Appl. No.: 787,640

[22] Filed: Jan. 23, 1997

[51] Int. Cl.⁶ .................................................. A61N 1/375
[52] U.S. Cl. ............................................................ 607/36
[58] Field of Search ................................... 607/36, 2, 9

[56] References Cited

U.S. PATENT DOCUMENTS

| | | | |
|---|---|---|---|
| 3,659,615 | 5/1972 | Enger | 607/36 |
| 3,918,460 | 11/1975 | King et al. | 607/36 |
| 3,943,937 | 3/1976 | King et al. | 607/36 |
| 4,041,955 | 8/1977 | Kelly et al. | 607/36 |
| 4,041,956 | 8/1977 | Purdy et al. | 607/36 |
| 4,243,042 | 1/1981 | Ware | 607/36 |
| 4,333,469 | 6/1982 | Jeffcoat et al. | 607/9 |
| 5,674,260 | 10/1997 | Weinberg | 607/36 |

*Primary Examiner*—William E. Kamm
*Assistant Examiner*—George R. Evanisko
*Attorney, Agent, or Firm*—Schwegman, Lundberg, Woessner & Kluth, P.A.

[57] ABSTRACT

An implantable medical device and method of making the same. The device includes an electronic component subassembly with an exterior surface. A plurality of electronic components are disposed spaced apart and internal to the external surface. The components define voids between one another. The voids are filled with an electrically insulative material which is substantially rigid. An ultra-thin hermetic shell is then formed over the exterior surface of the implantable medical device.

11 Claims, 3 Drawing Sheets

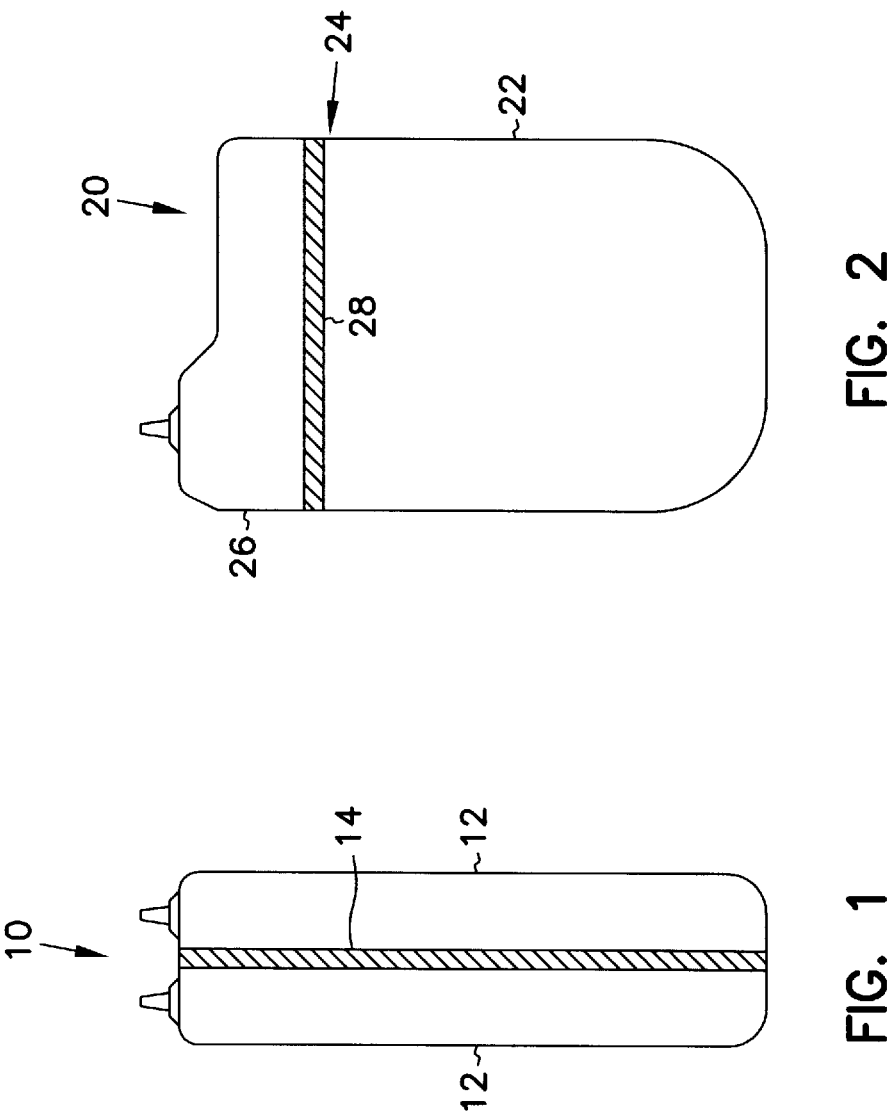

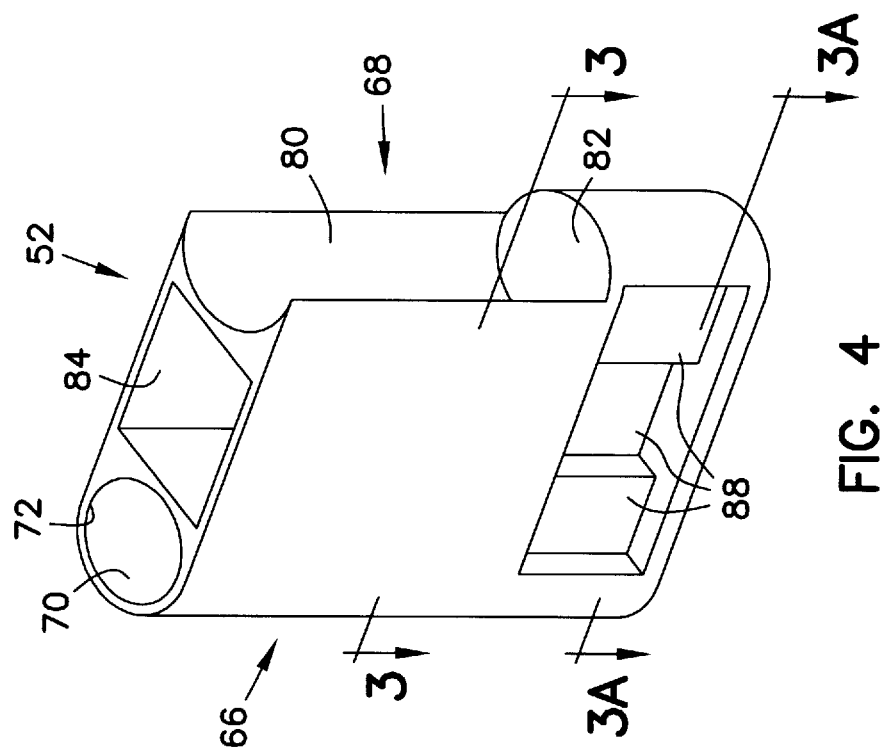
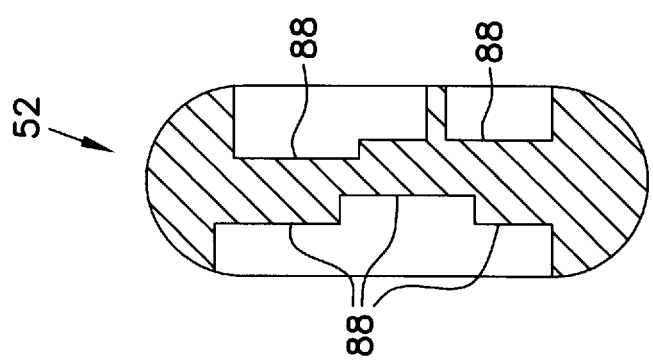
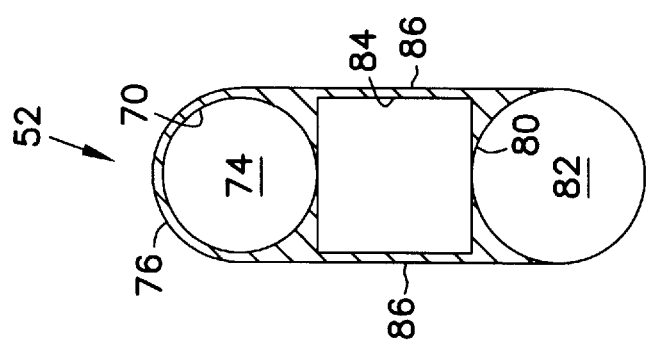

ULTRA-THIN HERMETIC ENCLOSURE FOR IMPLANTABLE MEDICAL DEVICES

FIELD OF THE INVENTION

The present invention relates to implantable medical devices and, more particularly, this invention relates to a device having an ultra-thin hermetic enclosure for reducing the overall weight and volume of the device.

BACKGROUND OF THE INVENTION

Pulse generators such as pacemakers or defibrillators implanted in the body for electrical cardioversion or pacing of the heart are well known. More specifically, devices implanted in or about the heart have been used to reverse (i.e., defibrillate or cardiovert) certain life-threatening arrhythmias, or to stimulate contraction (pacing) of the heart, where electrical energy is applied to the heart via electrodes to return the heart to normal rhythm. Devices have also been used to sense near the sinal node in the atrium of the heart and to deliver pacing pulses to the atrium. An electrode in the atrium positioned near the sinus node of the heart senses the electrical signals that trigger the heartbeat. The electrode detects abnormally slow (bradycardia) or abnormally fast (tachycardia) heartbeats. In response to the sensed bradycardia or tachycardia condition, a pulse generator or pacemaker produces corrective pulses or signals and delivers them to alleviate the condition.

The sick sinus syndrome and symptomatic AV block constitute the major reasons for insertion of cardiac pacemakers today. Cardiac pacing may be performed by the transvenous method or by electrodes implanted directly onto the ventricular epicardium. Transvenous pacing may be temporary or permanent. In temporary transvenous pacing, an electrode lead is introduced into a peripheral vein and fluoroscopically positioned against the endocardium of the right atrium or right ventricle. The proximal electrodes are connected to an external cardiac pacemaker which has an adjustable rate and milliamperage control. Temporary transvenous pacing is utilized (1) prior to the insertion of a permanent pacing system and (2) in situations in which the indication for pacing is judged to be reversible (drug-induced AV block or bradycardia) or possibly irreversible and progressive (AV and bundle branch blocks associated with myocardial infarction). Permanent transvenous pacing is performed under sterile surgical conditions. An electrode lead is generally positioned in the right ventricle or in the right atrium through a subclavian vein, and the proximal electrode terminals are attached to a pacemaker or defibrillator which is implanted subcutaneously. Another sense electrode may be positioned within the atrium of the heart near the sinus node.

The implanted pulse generator typically has a number of electronic components held within a sturdy case which both provides a hermetic and a protective enclosure for the electronics. The typical casing is constructed of titanium or stainless steel and has a wall thickness which is substantial enough to be relatively rigid providing structural integrity for the electronics as well. One type of case is a clamshell construction having two shallow concave case halves which define a perimeter parting line when mated together. The parting line is laser welded to close and seal the clamshell case. Another type of case is a deep drawn pocket type enclosure having an open end. The end is covered by a plate or end cap and again laser welded to the pocket enclosure. Because the case must provide both hermeticity and structural integrity for the device, a typical case accounts for about 5–10% of the volume of the device. Because the material is typically metallic and has a substantial wall thickness, the case also typically accounts for about 15–25% of the weight of the implant device. As today's electronics become smaller, these percentages have increased and will continue to do so accordingly.

Size and weight are two important concerns for implantable devices. It is desirable to reduce the weight and the size or volume of such devices wherever possible. The need for the case to provide structural integrity to the implantable device is what drives the minimum wall thickness of the case material. Therefore, if this requirement were eliminated, the size and weight of the case, and hence the implantable device, could be significantly reduced.

There is a real need for an implantable medical device such as a pacemaker or defibrillator having an ultra-thin hermetic case. A device equipped with such a thin enclosure would be of reduced size or volume. In addition, a device having an ultra-thin hermetic enclosure would be lighter in weight than a conventional implantable medical device.

SUMMARY OF THE INVENTION

An implantable medical device having a novel construction permitting utilization of an ultra-thin hermetic enclosure surrounding the internal components of the device. The device includes a plurality of electronic components held within a hermetic shell having an ultra-thin walled construction. The spaces between the various electronic components are filled with a suitably strong and lightweight material such as a thermoplastic or epoxy.

In one embodiment, a molded insert is produced having a particular shape for supporting and positioning the various electronic components. The components are added to the insert forming an electronic component sub-assembly. A hermetic shell is then added to the sub-assembly to seal the components therein.

In one alternative embodiment, the various electronic components are placed in a suitable mold and then potted with an epoxy material. The epoxy fills the voids or spaces between the components. After the epoxy is solidified, the mold is peeled away and an ultra-thin hermetic shell is again added.

In another alternative embodiment, the components are placed into a suitable injection mold cavity as inserts. A thermoplastic material is injected in liquid form into the mold and then cooled. The sub-assembly is removed from the mold and again hermetically sealed within an ultra-thin walled shell.

BRIEF DESCRIPTION OF THE DRAWINGS

FIG. 1 is a side view of a prior art implantable medical device having a clamshell case construction.

FIG. 2 is a front view of another prior art implantable medical device having a deep drawn pocket case construction.

FIG. 3 is a top cross-sectional view taken along line 3—3 of FIG. 4 the molded insert for an implantable medical device constructed according to the invention.

FIG. 3A is a top cross sectional view taken along line 3A—3A of FIG. 4.

FIG. 4 is a perspective view of the molded insert for an implantable medical device constructed according to the invention.

DESCRIPTION OF THE PREFERRED EMBODIMENT

Figure 8:
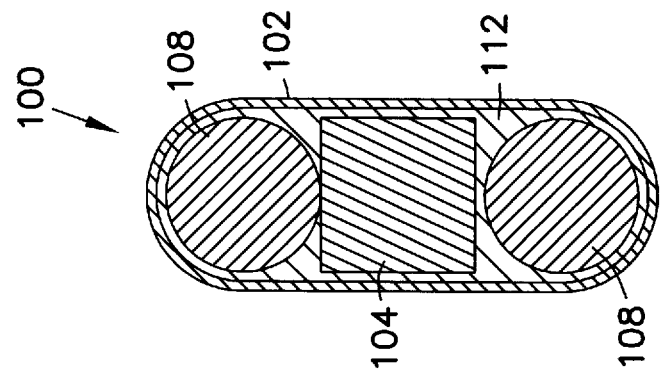
FIG. 8 is a top cross-sectional view of the component sub-assembly of FIG. 7 further including an ultra-thin hermetic shell.

In the following detailed description of the preferred embodiments, reference is made to the accompanying drawings which form a part hereof, and in which are shown by way of illustration specific embodiments in which the invention may be practiced. It is to be understood that other embodiments may be utilized and structural changes may be made without departing from the scope of the present invention.

FIGS. 1 and 2 each illustrate an appropriate view of a prior art implantable medical device such as a pulse generator. The device of FIG. 1 has a clamshell type case 10 having a pair of confronting concave halves 12 which, when mated, define a perimeter parting line 14. The parting line is laser welded to completely seal the electronic components (not shown) within the enclosure or case.

The device of FIG. 2 illustrates a case 20 having a deep drawn pocket enclosure 22 which has an open end 24 closed off by a cover 26. A parting line 28 is again defined between the two case portions and is again laser welded to seal the electronic components (not shown) within the enclosure or case.

Each of these typical prior art hermetic cases may be formed from a number of materials such as titanium, stainless steel or other bio-compatible material. The cases 10 and 20 are intended to provide two primary functions for the prior art implantable devices. The first is to hermetically seal the electronics within the case in an airtight environment. This is so that when the device is used subcutaneously in an individual, the components are not damaged by contact with body fluids. The second function is to provide structural integrity for the device to protect the electrical components held within the cases 10 and 20, respectively. The case must not deform or collapse when subjected to external compression forces during manufacture of the device, during an implant procedure, and once implanted within an individual.

A novel aspect of the invention is to provide a construction wherein the structural integrity of the device for protecting the electronic components is provided from within the device. The device's own internal construction prevents the device from permanent deformation or collapse when subjected to external compression forces or impact. Another novel aspect is that the invention permits reducing the outer case material thickness because the case no longer needs to provide the structural integrity for the device. Thus, the device of the invention has substantially reduced weight and volume when compared to the prior art designs.

Figure 6:
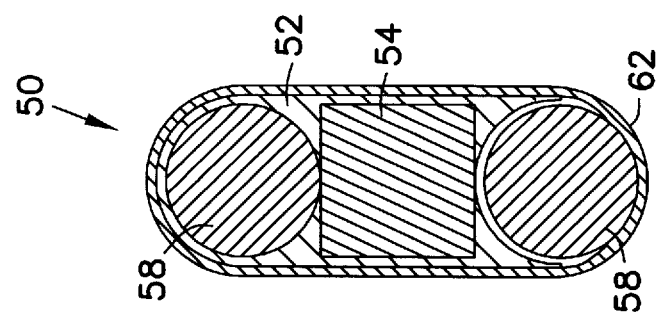
FIG. 6 is a top cross-sectional view of the component sub-assembly of FIG. 5 further including an ultra-thin hermetic shell.
Figure 5:
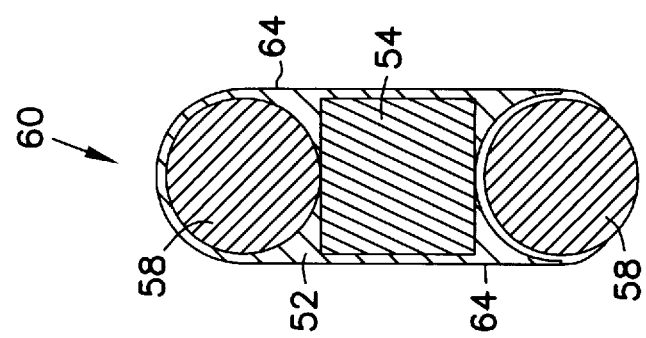
FIG. 5 is a top cross-sectional view of the molded insert of FIG. 4 after the various electronic components are added to form a component sub-assembly.

FIGS. 3–6 illustrate one embodiment of an implantable medical device 50 of the present invention. FIGS. 3 and 3A show a cross section of an insert 52 for supporting and carrying the internal electronic components of the implantable medical device 50. FIG. 4 shows insert 52 in a perspective view. The components are represented in FIG. 5 for illustrative purposes only as a battery 54 and a pair of capacitors 58 for delivering high energy defibrillating pulses. Most such devices also include various other electronic components such as printed circuit boards and the like. FIG. 5 illustrates a component sub-assembly wherein insert 52 carries the various components. FIG. 6 shows the device 50 including a hermetic shell 62 over the exterior surface 64 of sub-assembly 60.

In the present embodiment, insert 52 includes a pair of opposed ends 66 and 68 adapted to carry the capacitors 58 thereon. To illustrate the versatility of the invention, end 66 is shown having a blind bore 70 formed therein with an open end 72 and a closed end 74. An exterior wall 76 completely surrounds the bore 70. One of the capacitors 58 is inserted through open end 72 into the bore 70 until it bottoms out against closed end 74. As will be evident to those skilled in the art, the bore 70 and end 74 may include small openings or even connectors integrally molded in insert 52 to accommodate connection between the capacitors and other electronic components of the device. To protect the exposed end of capacitor 58, a cover may be inserted into open end 72 to close it off or the exposed end of capacitor 58 may be specifically designed to provide for its own impact protection.

End 68 of insert 52 illustrates another of the many possible constructions for supporting a capacitor 58. End 68 includes a concave surface 80 contoured to correspond to the exterior shape of the capacitor. A base member or surface 82 may be included, extending from the lower end of surface 80 to support one end of capacitor 58. With this construction, capacitor 58 must be designed to provide for its own protection, at least where exposed beyond the surfaces of the insert.

Insert 52 also includes a slot 84 formed to receive therein and to correspond in shape to another component such as battery 54. The slot 84 includes an outer wall 86 for protecting the component held within. Insert 52 further includes a pair of depressions 88 formed in its exterior surface for receiving other components such as a printed circuit board. The shape, depth and contour of depressions 88 may vary considerably, depending on the characteristics of the corresponding electronic components for which they are intended to support and carry. If such a depression is used, the component may be designed to include a protective surface to cover the exposed portion when inserted into depression 88.

Insert 52 of the present embodiment is preferably constructed from a lightweight, strong material such as thermoplastic and is injection molded or otherwise formed prior to assembly of the electrical components. As will be evident to those skilled in the art, the shape, size, contour and method of fabrication of insert 52 may vary considerably depending upon the particular application for which it is intended. Also, as mentioned above the insert may be molded to include passageways or integral connectors to provide for electronic communication between the various components of a particular device.

Additionally, a ribbed or flat wall may be used to span long open areas of insert 52 where a portion of a component is exposed, similar to outer wall 86 for battery 54 and exterior wall 76 for capacitor 58. Insert 52 may still provide for voids or spaces between components within the sub-assembly to save material and further reduce weight as long as the insert provides adequate structural integrity to support and protect the components. The purpose of insert 52 is simply to positively position the components within the hermetic shell once assembled and to protect the device from damage.

Once sub-assembly 60 is produced, the hermetic shell 62 is added to complete device 50, as shown in FIG. 6. One method would be to pre-fabricate a hermetic enclosure in two sections, similar to the clamshell case of FIG. 1 or the pocket case of FIG. 2, but where the sections each have an ultra-thin walled thickness or cross section. The electronic component sub-assembly 60 is inserted into the case prior to laser welding the two case sections together. Another method would be to plate or electroplate a thin layer of material such as titanium, stainless steel, or other bio-compatible material onto the sub-assembly. The thickness of the hermetic case 62 need only be sufficient to hermetically seal the electronic components held therein. The ultra-thin case 62 need not provide any structural support for protection of the components within the device because insert 52 and the components themselves provide such protection.

Figure 7:
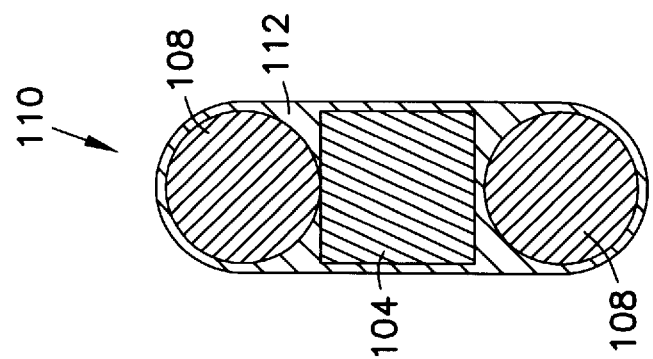
FIG. 7 is a top cross-sectional view of another embodiment of an implantable medical device component sub-assembly.

FIGS. 7 and 8 illustrate another embodiment of an implantable medical device 100 of the invention having an ultra-thin hermetic layer or shell 102. In this embodiment, the electronic components such as a battery 104, a printed circuit board (not shown) and a pair of capacitors 108 are again disposed fairly close to one another as shown in FIG. 7. Some spacing is necessary between the various components because of the variety of odd shapes in which they are available. The novel aspect of this embodiment is to mold a suitable material around the components to fill voids within and between the electronic components to form an essentially solid block or component sub-assembly 110. Again, the exterior dimensions of the sub-assembly are defined by the largest and strongest components of the electronic devices or by the outer layer of the molded material as shown in FIG. 7. By filling the voids with a suitable material which will not compress or deform when subjected to a compressive force, the need for an external, structural protective layer is eliminated. Thus, the only layer necessary over the exterior of the device is the airtight or hermetic shell 102.

Device 100 of FIG. 8 may be produced from one of several methods without departing from the scope of the invention. One such method includes potting the entire electronic component sub-assembly 110 prior to its insertion into the hermetic case 102. Potting involves the process of coating the internal components with an electrically insulative, lightweight epoxy 112. This is typically done by setting the components in a silicon mold. The epoxy is then introduced into the mold cavity and cured using light or a catalyst. The silicon mold is then peeled away leaving the components set in the epoxy as component sub-assembly 110. Potting the components fills the voids with epoxy 112 having relatively high strength when it is cured.

An alternative method would be to use the process known as insert injection molding. All of the electronic components are placed as inserts into an injection mold cavity. A material such as polypropylene or other suitable thermoplastic material is injected as a liquid into the cavity and then allowed to cool. The idea of this embodiment is again to eliminate the possibility of damage to the electronic components caused by an external compression force exerted on the device. This is accomplished by filling the voids or spaces with any suitable material which when solidified or cooled becomes substantially rigid and has adequate compressive strength. It is preferred that the material used to fill the voids is also lightweight so that the device is lighter than a conventional implantable device having a thick walled case. The ultra-thin hermetic case 102 of device 100 is then added to the exterior of the sub-assembly by one of several methods described above for device 50.

As an example, the typical structural case of FIGS. 1 and 2 may have wall thickness of about 0.016–0.025 inches (0.4–0.6 mm). A hermetic shell 62 or 102 of the invention which is produced as a clamshell or pocket construction may have a wall thickness of as little as 0.004–0.005 inches (0.10–0.12 mm). A plated hermetic shell may achieve a wall thickness of as little as about 0.001–0.002 inches (0.025–0.050 mm). Significant size reductions, material savings and substantial weight savings may be achieved utilizing the implantable medical device of the invention.

It is to be understood that the above description is intended to be illustrative, and not restrictive. Many other embodiments will be apparent to those of skill in the art upon reviewing the above description. The scope of the invention should, therefore, be determined with reference to the appended claims, along with the fall scope of equivalents to which such claims are entitled.

What is claimed is:

1. An implantable medical device, comprising:
    a component sub-assembly including an insert made of an electrically insulative material and a plurality of electronic components wherein the plurality of electronic components are attached to the insert; and
    a thin metal hermetic shell adapted to receive and encapsulate the component subassembly, the tin hermetic shell having a thickness of 0.012 inches or less,
    wherein the insert and one or more of the plurality of electronic components are configured so as to define an outer surface which conforms to an inner surface of the thin hermetic shell and which provides support for the thin hermetic shell.

2. The implantable medical device of claim 1, wherein said thin hermetic shell comprises a bio-compatible material.

3. The implantable medical device of claim 2 wherein said bio-compatible material comprises titanium or stainless steel.

4. The implantable medical device of claim 3, wherein said thin hermetic shell has a thickness of 0.005 inches or less.

5. The implantable medical device of claim 3, wherein said thin hermetic shell comprises a plated layer over the component sub-assembly.

6. The implantable medical device of claim 5, wherein said thin hermetic shell has a thickness of 0.002 inches or less.

7. The implantable medical device of claim 1, wherein the insert is an injection molded thermoplastic.

8. The implantable medical device of claim 1, wherein said insert is a preformed thermoplastic injection molded insert having a contour to adapt to support each of said plurality of electronic components.

9. A method of producing an implantable medical device, said method comprising:
    forming a component sub-assembly including an insert of electrically insulative material and a plurality of electronic components;
    placing said plurality of electronic components in a mold cavity;
    injecting a heated electrically insulative thermoplastic material around the plurality of electronic components within the mold cavity to form the component sub-assembly; and
    removing the component sub-assembly from the mold cavity when the thermoplastic material is sufficiently cooled;

encapsulating said component assembly in a thin hermetic shell; and where the insert and one or more of the plurality of electronic components define an outer surface of the component sub-assembly which conforms to an inner surface of the thin hermetic shell to provide support for the thin hermetic shell encapsulating the component sub-assembly.

10. A method of producing an implantable medical device, said method comprising:

forming a component sub-assembly including an insert of electrically insullative material and a plurality of electronic components, where the insert and one or more of the plurality of electronic components define an outer surface of the component sub-assembly which conforms to an inner surface of a thin hermetic shell to provide support for the thin hermetic shell encapsulating the component sub-assembly; and plating said component sub-assembly with a layer of bio-compatible material to form said thin hermetic shell.

11. A method of producing an implantable medical device, said method comprising:

forming a component sub-assembly including an insert of electrically insulative material and a plurality of electronic components, where the insert and one or more of the plurality of electronic components define an outer surface of the component sub-assembly which conforms to an inner surface of a thin hermetic shell to provide support for the thin hermetic shell encapsulating the component sub-assembly; and placing said component sub-assembly within a prefabricated hermetic casing and laser welding said prefabricated hermetic casing to form said thin hermetic shell.

* * * * *

UNITED STATES PATENT AND TRADEMARK OFFICE
CERTIFICATE OF CORRECTION

PATENT NO.: 5,876,424

DATED: March 2, 1999

INVENTOR(S): O'Phelan et al.

It is certified that error appears in the above-identified patent and that said Letters Patent is hereby corrected as shown below:

In column 6, line 25, delete "tin" and insert --thin--, therefore.
In column 7, line 12, delete "insullative" and insert -- insulative--, therefore.

Signed and Sealed this

Twenty-eighth Day of March, 2000

Attest:

Q. TODD DICKINSON

Attesting Officer

Commissioner of Patents and Trademarks